United States Patent [19]

Ward et al.

[11] 4,396,626
[45] Aug. 2, 1983

[54] CYCLIC COMPOUNDS AND THEIR USE

[75] Inventors: Robert W. Ward; Alexander C. Goudie, both of Harlow, England

[73] Assignee: Beecham Group Limited, England

[21] Appl. No.: 306,534

[22] Filed: Sep. 28, 1981

[30] Foreign Application Priority Data

Oct. 9, 1980 [GB] United Kingdom ................ 8032668

[51] Int. Cl.³ .................. A61K 31/40; C07D 207/333
[52] U.S. Cl. .................................... 424/274; 548/517; 548/518; 548/527; 548/539
[58] Field of Search ................. 548/517, 539; 424/274

[56] References Cited

U.S. PATENT DOCUMENTS 3,752,826  8/1973  Carson ........................... 548/539 X
4,048,191  4/1977  Carson ........................... 260/326.47
4,070,368  8/1978  Carson ........................... 260/326.47

FOREIGN PATENT DOCUMENTS 32048    7/1981  European Pat. Off.
1195628  3/1970  United Kingdom .
1327308  6/1973  United Kingdom .

OTHER PUBLICATIONS

J. Pharmacol. Exptl. Therap. 1973, 185, pp. 127–138.

Primary Examiner—Richard Raymond
Attorney, Agent, or Firm—Jacobs & Jacobs

[57] ABSTRACT

Compounds of the formula (I):

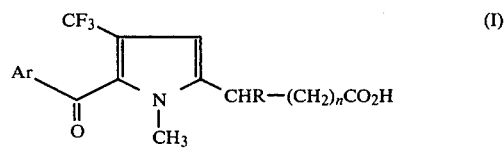

and pharmaceutically acceptable salts and pro-drugs thereof, wherein:
  Ar is a phenyl group optionally substituted by one or two moieties selected from halogen, $C_{1-4}$ alkyl, methoxy, methylthio or trifluoromethyl, or a 2-thienyl group or N-methyl-2-pyrryl group optionally substituted by one or two $C_{1-4}$ alkyl groups;
  R is hydrogen or methyl; and
  n is 0 or 1
having useful anti-inflammatory and/or analgesic activity, pharmaceutical compositions containing them, and processes for their preparation.

6 Claims, No Drawings

CYCLIC COMPOUNDS AND THEIR USE

The present invention relates to cyclic compounds having useful pharmacological activity, to processes for their preparation and to pharmaceutical compositions containing them.

Tolmetin, a clinically used anti-inflammatory and analgesic agent of the formula (A) (L=CH$_3$, Q=H):

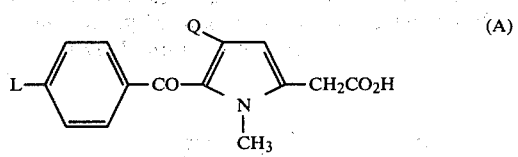

and zomepirac((A),L=Cl, Q=CH$_3$) and related compounds have been described in J. Pharmacol, Exptl. Therap. 1973, 185, 127–138, U.S. Pat. No. 3,752,826 and U.K. patent specification No. 1,195,628 and in U.K. patent specification No. 1,327,308 respectively. It has now been found that certain other arylacetic acids possess good anti-inflammatory and analgesic activity.

Accordingly, the present invention provides compounds of the formula (I):

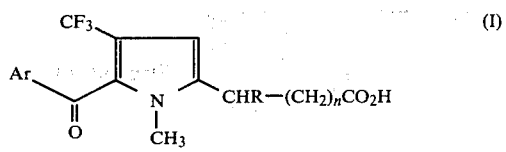

and pharmaceutically acceptable salts and pro-drugs thereof, wherein:

Ar is a phenyl group optionally substituted by one or two moieties selected from halogen, C$_{1-4}$ alkyl, methoxy, methylthio or trifluoromethyl, or a 2-thienyl group or N-methyl-2-pyrryl group optionally substituted by one or two C$_{1-4}$ alkyl groups;

R is hydrogen or methyl; and n is 0 or 1.

When used herein the term "pro-drug" means a compound metabolisable in vivo to a compound of the formula (I) or its salt. A pro-drug may be identified by administering the pro-drug to a mammal such as a rat, mouse, dog, monkey or man and identifying the compound of the formula (I) or its salt, in for example blood or urine.

One class of pro-drugs of the compounds of the formula (I) consists of in vivo hydrolysable esters. Such esters may be simple alkyl esters such as the methyl, ethyl, propyl or butyl esters, simply substituted alkyl esters such as the methoxymethyl, 2-methoxyethyl 2-hydroxyethyl or benzyl esters or other esters conventionally used in the medical arts as pro-drugs such as a C$_{1-4}$ acyloxymethyl, α-C$_{1-4}$ acyloxyethyl, C$_{1-4}$ alkoxycarbonyloxymethyl, α-C$_{1-4}$ alkoxycarbonyloxymethyl, or phthalidyl.

A further class of pro-drugs for the compounds of the formula (I) consists of in vivo hydrolysable amides thereof such as the primary amide, lower alkylamides and di-lower alkylamides thereof.

Another class of pro-drugs for the compounds of the formula (I) consists of the analogous compounds of lower oxidation state, namely the corresponding compounds in which the CO$_2$H groups is replaced by a CHO or CH$_2$OH group.

Particularly suitable classes of pro-drugs are those wherein the CO$_2$H group of the compound of the formula (I) is replaced by a group of the sub-formulae (a)–(k):

| | |
|---|---|
| —CH$_2$—CO—CH$_3$ | (a) |
| —CH$_2$—CHOH—CH$_3$ | (b) |
| —CHOH—CHOH—CH$_3$ | (c) |
| —CHOH—CO—CH$_3$ | (d) |
| —CH$_2$—CH(OCOR$_6$)—CH$_3$ | (e) |
| —CH=C(OR$_7$)—CH$_3$ | (f) |
| —CH—C(OR$_7$)=CH$_2$ | (g) |
| —CH$_2$—C(OR$_8$)OR$_9$—CH$_3$ | (h) |
| —CH$_2$—C(OCOR$_{10}$)=CH$_2$ | (i) |
| —CH=C(OCOR$_{10}$)—CH$_3$ | (j) |
| —CH$_2$—CH=CH$_2$ | (k) | wherein R$_6$ is a phenyl, substituted phenyl or C$_{1-4}$ alkyl optionally substituted by optionally substituted phenyl or amino; R$_7$ is a C$_{1-4}$ alkyl group; R$_8$ and R$_9$ are each C$_{1-4}$ alkyl groups or are joined to represent a CH$_2$CH$_2$ or CH$_2$CH$_2$CH$_2$ group; and R$_{10}$ is a C$_{1-4}$ alkyl group.

Particularly suitable examples of R$_6$ include methyl, ethyl, aminomethyl (salted by for example HCl); and phenyl. Preferably R$_6$ is methyl or amino methyl.

Suitable examples of R$_7$, R$_8$ and R$_9$ and R$_{10}$ include methyl and ethyl, more suitably methyl. R$_8$ and R$_9$ may also be joined as described.

Preferred pro-drugs are those containing sub-formulae (a), (b), (c), and (e) as defined above. These are respectively of formulae

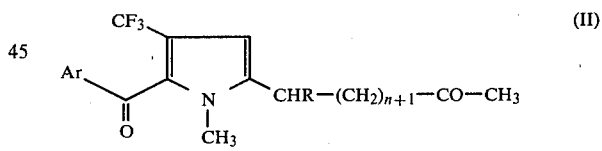

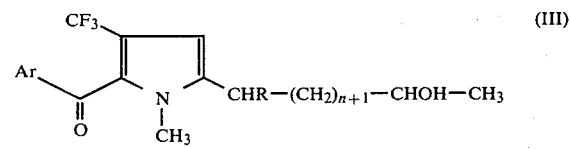

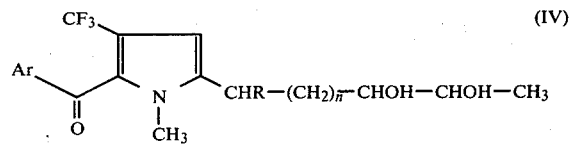

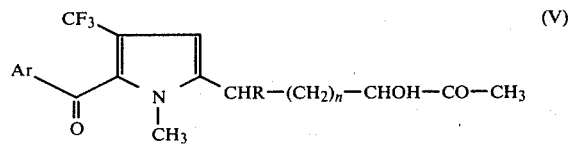

Certain preferred pro-drugs are those containing a group of the sub-formula (a), that is, compounds of the formula (II).

Apt pharmaceutically acceptable salts for the compounds of the formula (I) include alkali metal and alkaline earth metal salts, particularly the sodium, potassium, calcium and magnesium salts, and salts of pharmaceutically acceptable nitrogenous bases such as the ammonium salt and salts of protonated pharmaceutically acceptable amino acids, such as $H_3^+N.CH_2.COOH$.

In the compounds of the formula (I) and the pharmaceutically acceptable salts and pro-drugs thereof the optional substituents within the Group Ar may be the same or different and may be halogen or $C_{1-4}$ alkyl.

When a substituent is halogen it is usually chlorine or bromine. When two such substituents are halogen they will usually be the same.

When a substituent is $C_{1-4}$ alkyl, suitable examples thereof include methyl, ethyl and n- and iso-propyl, more suitably methyl. When two substituents are each $C_{1-4}$ alkyl they are usually the same.

R is preferably hydrogen.

n is preferably 0.

From the foregoing it will be realised that certain particularly suitable compounds of invention are those of the formula (VI):

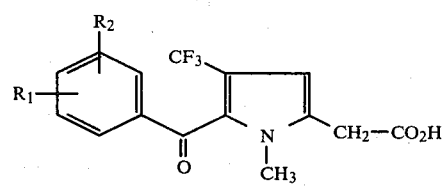
(VI)

wherein the $R_1$ and $R_2$ are independently hydrogen, halogen, $C_{1-4}$ alkyl, methoxy, methylthio or trifluoromethyl, pharmaceutically acceptable salts thereof and pro-drugs thereof of the formulae (VII), (VIII), (IX) and (X).

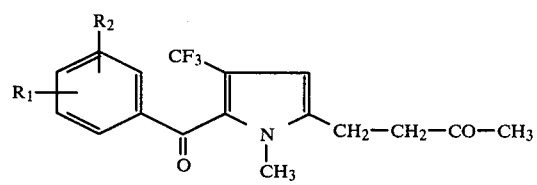
(VII)

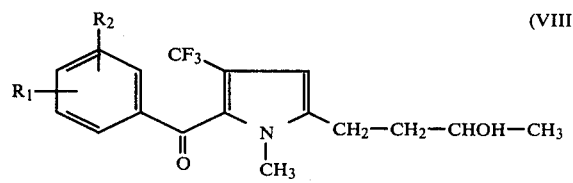
(VIII)

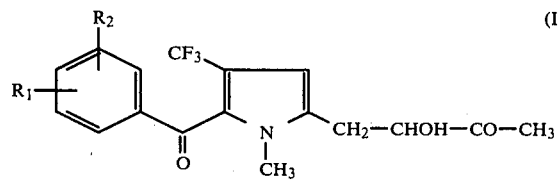
(IX)

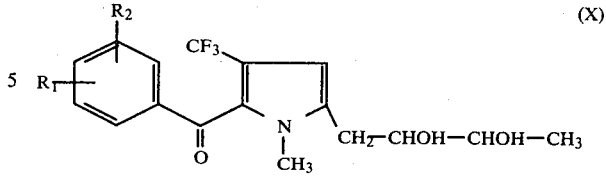
(X)

wherein the variables are as defined in formula (I).

A second group of compounds of the present invention of interest are those of the formula (XI):

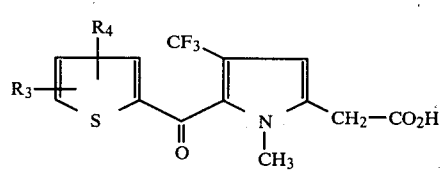
(XI)

wherein $R_3$ and $R_4$ are independently hydrogen or $C_{1-4}$ alkyl, pharmaceutically acceptable salts thereof and pro-drugs thereof of the formulae (XII), (XIII), (XIV) and (XV):

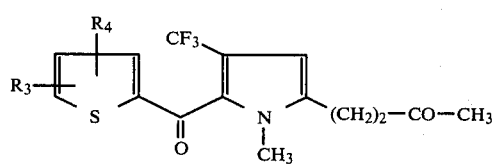
(XII)

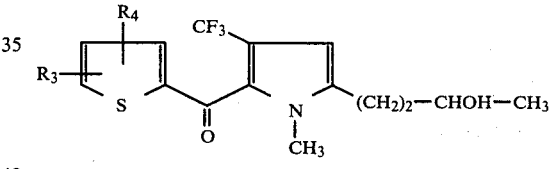
(XIII)

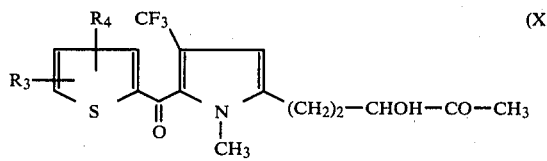
(XIV)

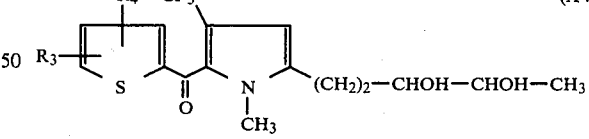
(XV)

A third group of compounds of the present invention of particular interest are those of the formula (XVI):

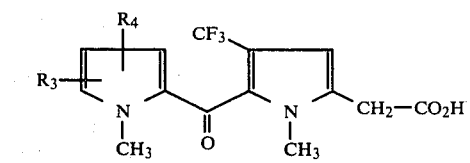
(XVI)

wherein $R_3$ and $R_4$ are as defined in formula (XI), pharmaceutically acceptable salts thereof and pro-drugs thereof of the formulae (XVII), (XVIII), (XIX) and (XX):

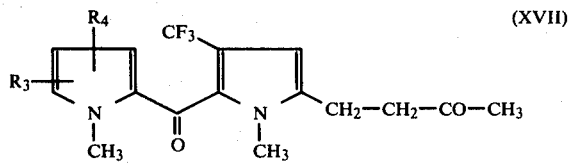
(XVII)

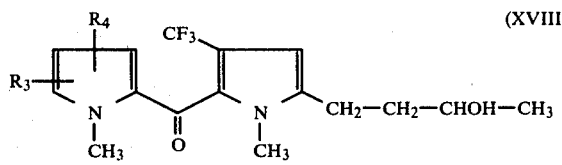
(XVIII)

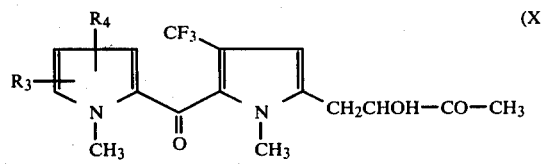
(XIX)

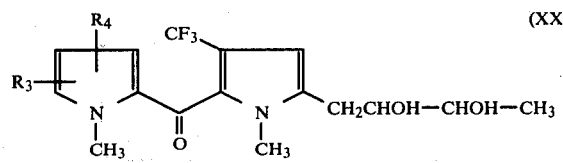
(XX)

wherein $R_3$ and $R_4$ are as defined in formula (XI):

It will be appreciated that compounds of the formula (I) wherein R is methyl and pharmaceutically acceptable salts and pro-drugs thereof have an asymmetric centre. The present invention extends to the enantiomers thereof and the racemates of these enantiomers.

It is believed that where the group Ar is sufficiently bulky, rotation about the pyrrole-CO axis can be sufficiently constrained to give rise to an asymmetric centre. The present invention extends to enantiomers of such compounds, and pharmaceutically acceptable salts and pro-drugs thereof and to racemates of such enantiomers. The invention also extends to all isomers, and mixtures thereof, of such compounds, salts and pro-drugs wherein R is methyl.

The compounds of the present invention are most suitably provided in crystalline form.

The present invention also provides a process for the preparation of a compound of the formula (I) or a pharmaceutically acceptable salt thereof, which process comprises the basic hydrolysis of a compound of the formula (XXI):

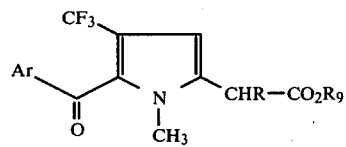
(XXI)

wherein:

Ar and R are as defined in formula (I); and $R_9$ is $C_{1-4}$ alkyl;

and thereafter if desired converting R when hydrogen in the resultant compound of the formula (I) to $C_{1-4}$ alkyl and if desired acidifying the resulting salt to form a compound of formula (I), or converting the salt to a pharmaceutically acceptable salt thereof, or to another pharmaceutically acceptable salt thereof.

Conversion of R when hydrogen to R $C_{1-4}$ alkyl may be carried out conventionally, for example by sequential reaction with an inorganic base and the relevant alkyl iodide in a polar inert solvent such as tetrahydrofuran. Suitable bases include sodium hydride. A preferred base is the combination of butyllithium and di-isopropylamine.

The hydrolysis may be effected using a hydroxide such as sodium hydroxide, in aqueous ethanol. The free acid of the formula (I) may be prepared by treating the resultant salt with hydrochloric acid or the like. Pharmaceutically acceptable salts of the compounds of the formula (I) may be prepared by ion exchange.

The following Scheme I shows synthetic pathways to compounds of the formula (I):

Scheme 1

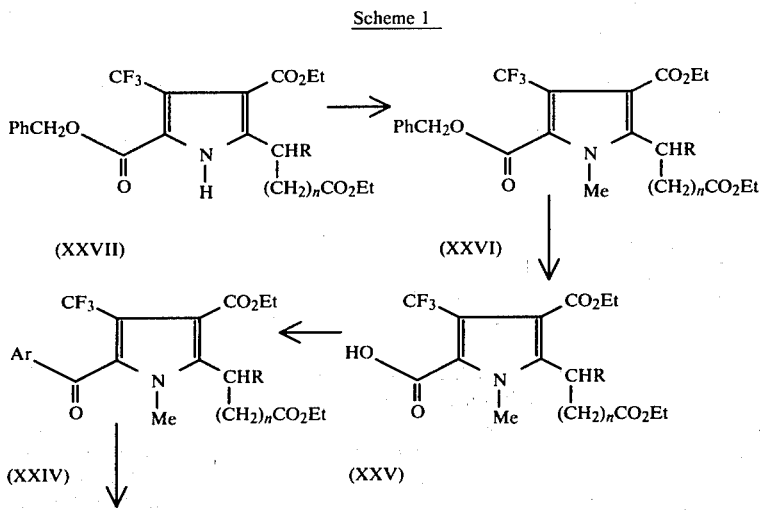

Scheme 1

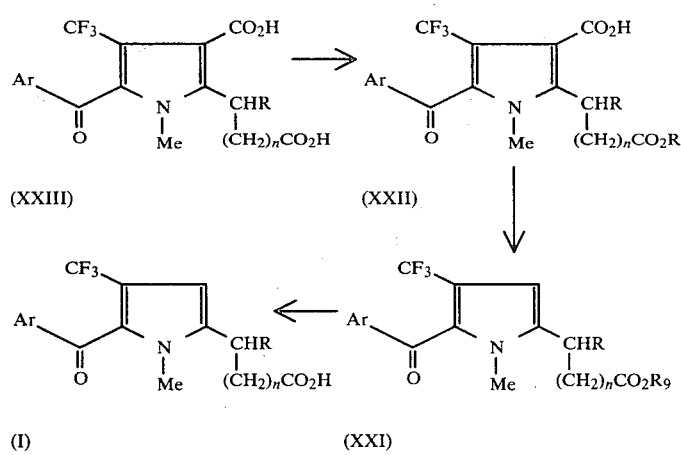

It is believed that compounds of the formulae (XXI) to (XXVII) are also novel, and as such intermediates of the formulae (XXI) to (XXVII) form an aspect of the present invention.

Intermediates of the formula (XXI) may be prepared by decarboxylation of a compound of the formula (XXII) (see Scheme I).

It is believed that decarboxylation cannot be effected by the conventional method of heating a pure melt of the compound of formula (XXII) at e.g. 210°–230° C. in an inert atmosphere for 2 hours, (see U.K. Patent Specification No. 1,327,308). Surprisingly we have now found that decarboxylation can be effected by heating with copper bronze in quinoline at 200°–220° C. for a shorter period (e.g. 20 minutes to 1½ hours dependent on temperature.

Compounds of the formula (XXII) are prepared from those of formula (XXIII) by analogy with known compounds.

Intermediates of the formula (XXIII) may be prepared by de-esterifying a compound of the formula (XXIV) (see Scheme I), under condition substantially as hereinbefore described for the de-esterification of compounds of the formula (XXI).

Compounds of the formula (XXIV) may be prepared by treating an activated derivative of, for example the acid chloride, of the compound of the formula (XXV) with an arylcopper (I) compound ArCu where Ar is as defined in formula (I). The compound ArCu may conveniently be prepared in situ by treating a corresponding arylmagnesium halide or aryllithium with a copper (I) halide such as the chloride.

The reaction is generally carried out at depressed temperatures e.g. −75° to 0° C., in an inert anhydrous aprotic solvent such as diethyl ether.

The present invention also provides a process for the preparation of a pro-drug of a compound of the formula (I) which is an in vivo hydrolysable ester thereof, which process comprises esterifying the compound of the formula (I) or active acylating derivative thereof with the corresponding alcohol.

Esterification of the acid itself may be carried out in conventional manner, for instance under acid catalysis and/or under reflux in an inert solvent having a non-extreme boiling point such as less than 100° C. Alternatively it may be carried out in the presence of a dehydrating agent such as dicyclohexylcarbodiimide.

The present invention additionally provides processes for the preparation of a pro-drug of a compound of the formula (I) which is an in vivo hydrolysable amide thereof, which process comprises reacting an active derivative of the compound of the formula (I) with ammonia or a corresponding amine.

Suitable active acylating derivatives of the acid of the formula (I) for esterification and amidation include acid halides such as the acid chloride, the acid anhydride, mixed anhydrides such as those formed from ethyl chloroformate and esters such as the methyl and ethyl esters.

The reactions are normally carried out in nonhydroxylic organic solvent such as tetrahydrofuran, ethyl acetate, toluene, dichloromethane or NN-dimethylformamide. Esterification is normally carried out in the presence of an acid acceptor such as pyridine or triethylamine. The reactions may be carried out at any non-extreme temperature such as −10°–100° C. and more suitably 0°–80° C., for amidation most suitably 10°–50° C. The higher reaction temperatures are employed with less active derivatives of the acid of the formula (I) such as esters whereas the lower temperatures are employed with the more reactive derivatives of the acid of the formula (I) such as mixed anhydrides.

The present invention further provides a process for the preparation of a pro-drug of a compound of the formula (I) in which the $CO_2H$ group is replaced by a CHO group, which process comprises the reduction of an acid halide of the compound of the formula (I).

The reaction may be suitably carried out under Rosenmund reduction conditions, that is with hydrogen using a palladium/barium sulphate catalyst in an inert organic solvent. A small amount of quinoline and sulphur may be added. Suitable solvents include anhydrous acetone, ethyl acetate and xylene. The reaction may be carried out at a temperature in the range 10° to 150° C.

Tri-n-butyl tin hydride may also be used as a reductant.

The present invention provides a process for the preparation of a pro-drug of a compound of the formula (I) in which the $CO_2H$ group is replaced by a $CH_2OH$ group which process comprises the reduction of a compound of the formula (I) in which the $CO_2H$ group has been replaced by a CHO group.

This reaction may be suitably carried out with a mild complex hydride such as sodium borohydride or a structurally hindered complex hydride such as lithium tri-t-butoxyaluminium hydride. Reaction is usually carried out in a solvent conventionally regarded as compatible with the reductant used at a non-extreme temperature such as $-30°$ to $80°$ C., more suitably $-10°$ to $60°$ C., depending on the reductant employed.

The prodrug which is a compound of formula (I) wherein $CO_2H$ is replaced by a $CH_2COCH_3$ sub-formula (a) group (i.e. of formula (II)) may be prepared by the oxidation of a compound of the formula (I) wherein $CO_2H$ is replaced by a sub-formula (k) group; that is, of formula (XXVIII):

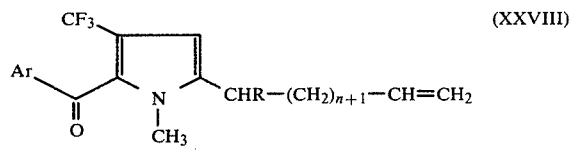

wherein the variables are as defined in formula (I).

The oxidation is suitably carried out in aqueous dimethylformamide solution in the presence of palladium chloride and cuprous chloride using pure oxygen or air. In general it is sufficient to blow air through the reaction mixture at an ambient or slightly elevated temperature to effect oxidation. The desired compound may be obtained from the reaction mixture by dilution with water followed by extraction into a water-immiscible solvent such as chloroform which may then be dried and evaporated. This initial crude material may be purified chromatographically if desired, for example by column chromatography on silica gel using 1:1 ether:petrol eluant.

Prodrugs of the formula (II) may also be prepared from the corresponding pro-drugs containing the group of sub-formula (g) $CH_2—C(OR_7)=CH_2$, i.e. of formula (XXIX):

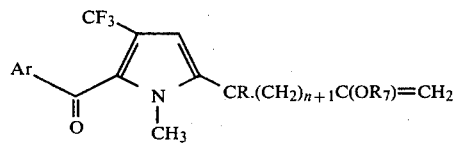

for example by stirring in dilute acid.

The pro-drugs of the formula (II) may also be prepared by thermal decomposition of a compound of formula (XXX):

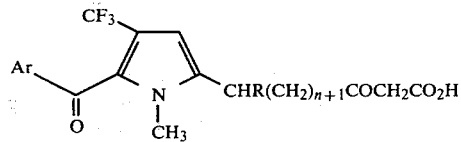

This decomposition may suitably be carried out with or without an inert solvent, such as dimethyl sulphoxide, at about 60° to 100° C.

The intermediates of formula (XXX) may themselves be prepared from a compound of formula (I) wherein $n=1$ or 2 via a suitably activated derivative such as the ethoxycarbonyl derivative, for example following the general method described in Synthesis 1979, p. 787.

It will be appreciated that the compounds of formula (I) wherein $n=1$ or 2 may be prepared in analogous manner to the preparation of the corresponding compounds of formula (I) wherein $n=0$ except that dimethyl 3-oxoadipate or dimethyl 3-oxopimelate are suitably used in the Knorr pyrrole synthesis reaction. Compounds of formula (II) wherein $R=Me$ may also be prepared in analogous manner using dimethyl 4-methyl-3-oxoadipate or dimethyl 4-methyl-3-oxopimelate in the Knorr pyrrole synthesis reaction.

Compounds of the formula (I) wherein the $CO_2H$ group is replaced by a group of the sub-formula (b), that is, of formula (III) may be prepared by the reduction of a corresponding compound of the formula (I) wherein the $CO_2H$ group is replaced by a group of the sub-formula (a), that is, of formula (II). Such a reaction may use a complex hydride such as sodium borohydride. Mild conditions and avoidance of excess reagent prevent reduction of the bridging carbonyl.

Compounds of the formula (I) wherein the $CO_2H$ group is replaced by a group of the sub-formula (c); that is, of formula (XXXI):

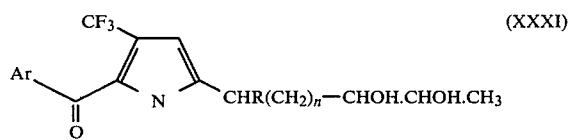

may be prepared by reduction of a corresponding compound of the formula (I) in which the $CO_2H$ group is replaced by a group of the sub-formula (d), that is, of formula (V). Such a reaction may be effected using sodium borohydride under conventional conditions.

Compounds of the formula (I) wherein the $CO_2H$ group is replaced by a group of the sub-formula (d), $CH_2CHOHCOCH_3$, that is, of formula (V):

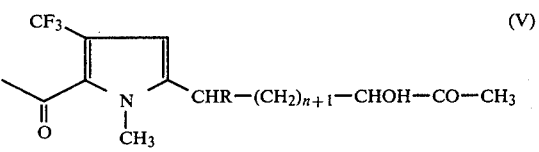

may be prepared by the oxidation of a compound containing sub-formula (f), $CH=C(OR_7)CH_3$, that is of formula (XXXII):

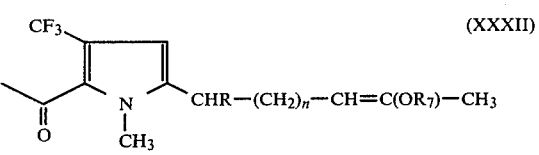

Such oxidations are generally carried out with m-chloroperbenzoic acid at $0°–5°$ C. in mixed solvents such as diethyl ether/water.

Compounds of the formula (I) wherein the $CO_2H$ group is replaced by sub-formula (e), that is of formula (XXXIII):

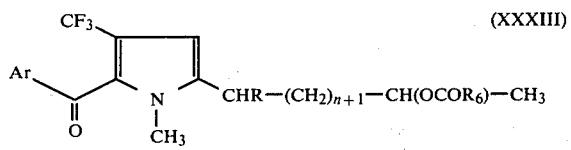

be prepared by the acylation of a corresponding compound containing the sub-formula (b), that is, of formula (III). Methods of acylation include those described in Belgian Pat. No. 854 429 (U.K. Pat. No. 1 538 473).

Compounds of the formula (I) wherein the $CO_2H$ group is replaced by sub-formula (f) or (g), that is, of formula (XXXII) or (XXIX):

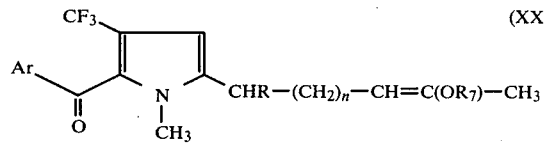
(XXXII)

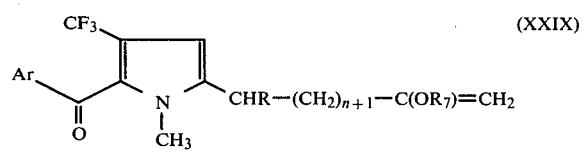
(XXIX)

may be prepared by enol etherification of a compound containing the sub-formula (a), i.e. of formula (II). Methods of enol etherification include those described in DE-OS No. 2647966.3 or U.S. Pat. No. 4,180,585 and in BE 866,857 or U.S. Pat. No. 4,200,645.

A further process for the preparation of a compound of formula (XXIX) comprises decarboxylating a compound of formula (XXXIV):

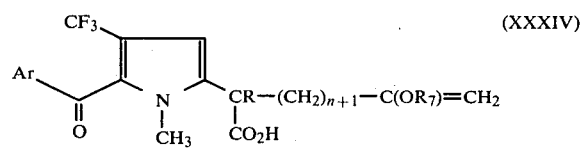
(XXXIV)

Compounds of formula (XXXIV) may be prepared by the alkoxyallylation of a compound of formula (I) suitably for example with 2-methoxyallylbromide. The decarboxylation of compounds of formula (XXXIV) suitably is carried out in analogous manner to the decarboxylation of a compound of formula (XXX) as hereinbefore described.

The preparation and decarboxylation of compounds of formula (XXXIV) may suitably be carried out analogously to the preparation and decarboxylation of a compound of formula (XXXVIII) hereinafter.

Salts of pro-drugs, when appropriate, can be prepared in conventional manner.

Compounds containing the moiety of sub-formula (h), that is of formula (XXXV):

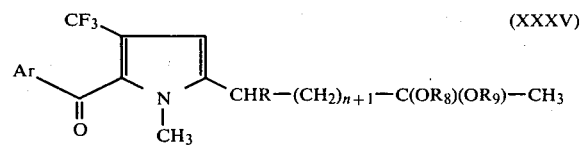
(XXXV)

may be prepared by acetalation of a corresponding formula (II) compound. Apt methods include those of DE-OS No. 2647966.3 or U.S. Pat. No. 4,180,585.

Compounds of the formula (I) wherein the $CO_2H$ group is replaced by sub-formula (i) or (j), that is, of formula (XXXVI) or (XXXVII):

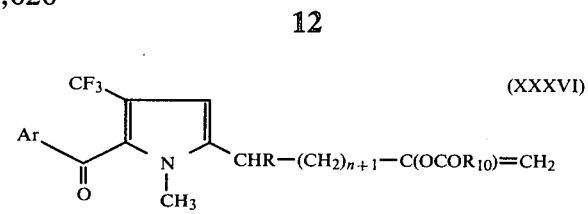
(XXXVI)

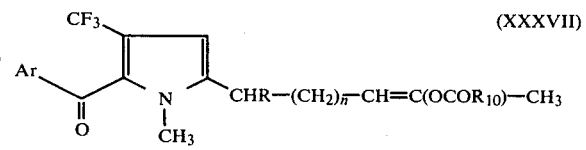
(XXXVII)

may be prepared by enol esterification of the corresponding formula (II) compound. Apt methods include those of DE-OS No. 2647966.3 or U.S. Pat. No. 4,180,585.

The prodrug which is a compound of formula (I) wherein $CO_2H$ is replaced by a sub-formula (k) $CH_2CH=CH_2$ group, that is of formula (XXVIII) may be prepared by the decarboxylation of a corresponding compound of the formula (XXXVIII):

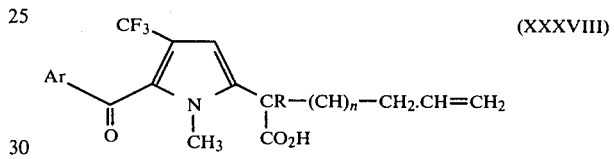
(XXXVIII)

wherein the variables are as hereinbefore defined.

The decarboxylation may be effected by heating with Cu/quinoline for example to 170°–210° C. The desired product may be obtained by trituration under a non-hydroxylic solvent such as chloroform.

The acid of the formula (XXXVIII) may be obtained by hydrolysis of the corresponding $C_{1-4}$ alkyl ester such as the ethyl ester using normal sodium hydroxide solution followed by neutralisation with hydrochloric acid. This $C_{1-4}$ alkyl ester may be prepared by the allylation of the corresponding compound of the formula (I). Such allylations may be brought about by generating an anion of the compound of formula (I), for example with sodium hydride in dimethoxyethane, and quenching the said anion with allyl bromide or 4-bromobut-1-ene as appropriate.

Alternatively, compounds of the formula (XXXVIII) may be prepared by the direct allylation of a compound of formula (I), with for example allyl bromide or 4-bromobut-1-ene in the presence of lithium diisopropylamide.

The alkyl ester of a compound of the formula (XXXVIII) wherein R is a methyl group may alternatively be prepared by methylation of the corresponding ester wherein R is a hydrogen atom, for example be sequential reaction with sodium hydride and methyl iodide.

The enantiomers of compounds of the formula (I) of the types described hereinbefore and pharmaceutically acceptable salts and pro-drugs thereof may be resolved from their racemates by conventional resolution techniques.

Stereoisomers of the types described hereinbefore may be separated conventionally, e.g. by chromatography.

In a further aspect this invention provides a pharmaceutical composition which comprises a compound of the formula (I) or a pharmaceutically acceptable salt or pro-drug thereof, and a pharmaceutically acceptable carrier.

The compositions of this invention are useful in treating rheumatic and arthritic conditions because of their anti-inflammatory and analgesic properties. The compositions may be adapted for administration via the topical oral, rectal or injection routes but it is preferred that they are adapted for oral administration.

The compositions of this invention may contain diluents, binders, fillers, disintegrants, flavouring agents, colouring agents, lubricants, preservatives or the like in conventional manner. These conventional excipients may be employed in conventional manner, for example as in the preparation of compositions of ketoprofen, indomethacin, naproxen, acetylsalicylic acid or other anti-inflammatory analgesic agents.

Most suitably the composition of this invention will be in the form of a unit dose such as a tablet, capsule or reconstitutable powder in a sachet. Such unit doses will generally contain from 10 mg to 1000 mg and more suitably will contain from about 30 mg to 500 mg for example 50 mg to 250 mg of active agent, for example about 50, 100, 150, 200, 250, 300, 350, 400, 450 or 500 mg. These compositions may be administered once or more times a day, for example 2, 3 or 4 times daily, so that the total daily dose for a 70 kg adult will usually be in the range of 200 to 3000 mg and more usually in the range 300 to 3000 mg for example 500 to 2000 mg. Alternatively the unit dose may contain from 2–20 mg of active agent and may be administered in multiples if desired to give the preceeding daily dose.

A favoured form of the composition of this invention is a hard gelatin capsule containing the active agent. The active agent may be in the form of a powder, granulate or the like and may advantageously be in intimate mixture with a lubricant such as magnesium stearate.

A further favoured form of the composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

This present invention also provides a method of treating inflammatory and/or painful conditions in mammals which comprises administering to the sufferer a therapeutically effective dose of a compound of the formula (I) or a pharmaceutically acceptable salt or a prodrug thereof. Suitable doses for such a compound per day are from 50 to 4000 mg of a compound of this invention and more usually from 100 to 3000 mg for example from 200 to 1500 of a compound of this invention.

Mammals which may be thus treated include humans and domestic animals such as dogs, cats or horses.

Most suitably the medicament will be administered orally as 2, 3 or 4 doses per day at the dose level previously indicated.

The following Example illustrates the preparation of the compounds of the present invention, and the following Descriptions illustrate the preparation of intermediates thereto.

DESCRIPTION 1

Benzyl 3-oxo-4,4,4-trifluorobutyrate (D1)

Ethyl 3-oxo-4,4,4-trifluorobutyrate (25 g, 0.136 mole) was heated between 100° and 180° C. under nitrogen with benzyl alcohol (14 ml, 0.136 mole) for 3 hours, the ethanol formed being distilled from the reaction mixture. The resulting pale yellow oil was distilled under vacuum to give a colourless oil (26.1 g, 78%), b.p. 81°–82° C. at 0.20 mm Hg.

DESCRIPTION 2

5-Benzyl diethyl 4-trifluoromethylpyrrole-2-acetate-3,5-dicarboxylate (D2)

Sodium nitrate (9.19 g, 0.138 mole) in tap water (16 ml) was added dropwise 5° and 7° C. over 40 minutes to a vigorously stirring solution of the above benzyl ester (26.3 g, 0.0106 mole) in glacial acetic acid (110 ml). After completing the addition the mixture was stirred at 0° C. for a further 15 minutes and then for 2 hours at room temperature. Diethyl acetone-1,3-dicarboxylate (19.9 ml, 0.106 mole) was added and temperature taken up to 65° C. and then maintained below 75° C. by cooling as zinc powder (21.8 g, 0.320 mole) was added portionwise. After this addition the mixture was refluxed for 1½ hours before pouring into a vigorously stirring mixture of ice water (3 liters). A sticky yellow crystalline solid formed in about 15 minutes and this was filtered off, washed with water, dried and recrystallised from 2:1 petrol:toluene mixture to give a white crystalline solid (13.0 g, 29%) m.p. 114°–117° C., n.m.r. $\delta(CDCl_3)$ 10.7 (1H, br., s), 7.27 (5H, s), 5.23 (2H, s), 4.22 (2H, q, J=7 Hz), 4.11 (2H, q, J=7 Hz), 3.87 (2H, s), 1.31 (3H, t, J=7 Hz) and 1.23 (3H, t, J=7 Hz).

DESCRIPTION 3

5-Benzyl diethyl 1-methyl-4-trifluoromethylpyrrole-2-acetate-3,5-dicarboxylate (D3)

The above pyrrole triester (13.0 g, 0.030 mole) was refluxed in ethylmethylketone (250 ml) for 2 hours with anhydrous potassium carbonate (10.7 g, 0.080 mole) and dimethyl sulphate (5.8 ml, 0.060 mole) and then cooled and poured into water (500 ml).

The solution was extracted with ether (2×200 ml), the organic layer then washed with water (2×100 ml), 1 M ammonium hydroxide solution (100 ml) to remove excess dimethyl sulphate, water again (1×100 ml), dried (anhydrous $Na_2SO_4$) and concentrated to leave a red oil (11.9 g, 90%), n.m.r. $\delta(CCL_4)$ 7.23 (5H, s), 5.18 (2H, s), 4.16 (2H, q, J=7 Hz), 4.04 (2H, q, J=7 Hz), 3.85 (2H, s), 3.55 (3H, s), 1.28 (3H, t, J=7 Hz) and 1.22 (3H, t, J=7 Hz).

DESCRIPTION 4

Diethyl 1-methyl-4-trifluoromethylpyrrole-2-acetate-3-carboxylate-5-carboxylic acid (D4)

The above N-methylpyrrole triester (11.9 g, 0.027 mole) was hydrogenated at atmospheric pressure over 1 hour with 10% Pd/C (1.0 g) in ethyl acetate (500 ml). The catalyst was filtered off, washed with methanol and the filtrate concentrated to give a quantitative yield of pale yellow solid, n.m.r. $\delta(CCl_4)$ 11.43 (1H, br., s), 4.17 (2H, q, J=7 Hz), 4.06 (2H, q, J=7 Hz), 3.88 (2H, s), 3.65 (3H, s), 1.28 (3H, t, J=7 Hz) and 1.22 (3H, t, J=7 Hz).

DESCRIPTION 5

Diethyl 5-p-chlorobenzoyl-1-methyl-4-trifluoromethylpyrrole-2-acetate-3-carboxylate (D5)

A solution of 4-bromochlorobenzene (15.3 g, 0.08 mole) in dry ether (35 ml) was added dropwise to magnesium turnings (2.88 g, 0.12 mole) in dry ether (12.5 ml) under nitrogen at such a rate as to maintain a steady reflux. After completing addition the solution was refluxed for a further 30 minutes to produce a pale brown solution. A sample of this p-chlorophenyl magnesium bromide solution (100 ml, 0.048 mole) was then added dropwise to a suspension of cuprous iodide (10.10 g, 0.053 mole) in dry ether (80 ml) under nitrogen at 0° C. and resulting brown solution allowed to warm to 10° C. over 10 minutes. On cooling to −78° C. a solution of the pyrrole acid chloride (0.016 mole) in dry ether (60 ml), prepared from the above pyrrole acid (5.60 g, 0.016 mole) and oxalyl chloride (2.8 ml, 0.032 mole) in refluxing toluene (200 ml) over 2 hours, was added dropwise over 40 minutes and the reaction miixture was then allowed to warm up to room temperature and stirred overnight. The resulting thick brown solution was poured into ice/dilute aqueous hydrochloric acid (200 ml) and extracted with ether (2×200 ml). The organic layer was washed successively with saturated sodium bicarbonate solution (2×100 ml), aqueous 3-dimethylaminopropylamine (2×100 ml), dilute aqueous hydrochloric acid (2×100 ml), sodium bicarbonate solution again (1×100 ml) and water (1×100 ml) before being dried (anhydrous NaSO4) and evaporated to dryness to leave a brown oil. This was purified by column chromatography using silica gel (250 g) and 1:1 petrol:ether as eluant to give a yellow oil as product (6.12 g, 85%), n.m.r. $\delta(CCl_4)$ 7.71 (2H, d, J=9 Hz), 7.34 (2H, d, J=9 Hz), 4.22 (2H, q, J=7 Hz), 4.11 (2H, q, J=7 Hz), 4.05 (2H, s,), 3.38 (3H, s), 1.32 (3H, t, J=7 Hz) and 1.25 (3H, t, J=7 Hz).

Diethyl 5-(3'-methylbenzolyl)-1-methyl-4-trifluoromethylpyrrole-2-acetate-3-carboxylate (D6) was prepared analogously.

n.m.r.: $\delta(CDCl_3)$: 7.9–7.0 (4H, m), 4.5–3.9 (4H, overlapping quartets, J=7 Hz), 4.1 (2H, s), 3.43 (3H, s), 1.6–1.1 (6H, overlapping triplets, J=7 Hz).

Diethyl 5-(4'-methylbenzoyl)-1-methyl-4-trifluoromethylpyrrole-2-acetate-3-carboxylate (D7), diethyl 5-(4'-methoxybenzoyl)-1-methyl-4-trifluoromethylpyrrole-2-acetate-3-carboxylate (D8), diethyl 5-(3'-trifluormethylbenzoyl)-1-methyl-4-trifluoromethylpyrrole-2-acetate-3-carboxylate (D9), and diethyl 5-(2-thienoyl)-1-methyl-4-trifluoromethylpyrrole-2-acetate-3-carboxylate (D10) are prepared analogously.

DESCRIPTION 6

5-p-Chlorobenzoyl-1-methyl-4-trifluoromethylpyrrole-2-acetic acid-3-carboxylic acid (D11)

The above diethyl ester (6.69 g, 0.015 mole) was refluxed with 25% aqueous sodium hydroxide (150 ml) and ethanol (50 ml) for 2 hours. The resulting solution was cooled, diluted with water (200 ml) and washed with ether (2×100 ml), before acidifying with dilute hydrochloric acid. The resulting precipitate was filtered off, washed with water and dried to yield an off-white solid as product, n.mr. $\delta(d^6\text{-DMSO})$ 7.50 (2H, d, J=8 Hz), 7.75 (2H, d, J=8 Hz), 7.3–6.0 (2H, br., s), 4.12 (2H, s) and 3.42 (3H, s).

5-(3'-chlorobenzoyl)-1-methyl-4-trifluoromethylpyrrole-2-acetic acid-3-carboxylic acid (D12) was prepared analogously.

n.m.r.: $\delta(DMSO-d_6)$: 7.7–7.3 (4H, m), 4.05(2H, s), 3.32 (3H, s), 12.5 (2H, br, s).

5-(4'-methylbenzoyl)-1-methyl-4-trifluoromethylpyrrole-2-acetic acid-3-carboxylic acid (D13), 5-(4'-methoxybenzoyl)-1-methyl-4-trifluoromethylpyrrole-2-acetic acid-3-carboxylic acid (D14), 5-(3'-trifluoromethyl)-1-methyl-4-trifluoromethylpyrrole-2-acetic acid-3-carboxylic acid (D15)

5-(2-thienoyl)-1-methyl-4-trifluoromethylpyrrole-2-acetic acid-3-carboxylic acid (D16) are prepared analogously.

DESCRIPTION 7

Ethyl 5-p-chlorobenzoyl-1-methyl-4-trifluoromethylpyrrole-2-acetate-3-carboxylic acid (D17)

A suspension of the above diacid (4.05 g, 0.010 mole) was refluxed with 0.5% ethanolic HCl (52 ml) for 1½ hours by which time a clear solution was formed. On cooling, the solution was poured into water (200 ml) and extracted with ether (2×150 ml), the organic layer then being washed with water (1×100 ml), dried (anhydrous Na2SO4) and concentrated to leave a yellow solid (4.09 g, 94%) m.p. 197°–199° C., n.m.r. $\delta(CDCl_3)$ 7.69 (2H, d, J=9 Hz), 7.37 (2H, d, J=9 Hz), 4.13 (2H, s), 4.11 (2H, q, J=Hz), 3.38 (3H, s) and 1.25 (3H, t, J=7 Hz).

Ethyl 5-(3'-chlorobenzoyl)-1-methyl-4-trifluoromethylpyrrole-2-acetic-3-carboxylic acid (D18) was prepared analogously.

n.m.r.: $\delta(DMSO-d_6)$: 7.8–7.35 (4H, m), 4.12 (2H, s), 4.02 (2H, q, J=7 Hz), 3.35 (3H, s), 1.16 (3H, t, J=7 Hz).

Ethyl 5-(4'-methylbenzoyl)-1-methyl-4-trifluoromethylpyrrole-2-acetate-3-carboxylic acid (D19), ethyl 5-(4'-methoxybenzoyl)-1-methyl-4-trifluoromethylpyrrole-2-acetate-3-carboxylic acid (D20), ethyl 5-(3'-trifluoromethylbenzoyl)-1-methyl-4-trifluoromethylpyrrole-2-acetate-3-carboxylic acid (D21), and ethyl 5-(2-thienoyl)-1-methyl-4-trifluoromethylpyrrole-2-acetate-3-carboxylic acid (D22) are prepared analogously.

DESCRIPTION 8

Ethyl 5-p-chlorobenzoyl-1-methyl-4-trifluoromethylpyrrole-2-acetate (D19)

The above acid (200 mg, 0.48 mmole) was heated in quinoline (2 ml), which had been dried over CaH, containing copper bronze (200 mg) at 210° C. under nitrogen for 20 minutes. When cool, the reaction mixture was poured into dilute hydrochloric acid (30 ml) and extracted with ether (2×50 ml). The organic layer was washed with sodium bicarbonate solution (2×30 ml), water (2×30 ml), dried (anhydrous Na2SO4) and evaporated to dryness to yield a brown oil. This was purified by column chromatography on silica gel (10 g) using 1:1 petrol:ether as eluant (70%), n.m.r. $\delta(CCl_4)$ 7.63 (2H, d, J=8 Hz), 7.28 (2H, d, J=8 Hz), 6.23 (1H, s), 4.07 (2H, q, J=7 Hz), 3.55 (2H, s), 3.48 (3H, s) and 1.22 (3H, t, J=7 Hz).

Ethyl 5-(3'-chlorobenzoyl)-1-methyl-4-trifluoromethylpyrrole-2-acetate (D24) was prepared analogously.

n.m.r.: δ(CDCl₃): 7.9–7.0 (4H, m), 6.31 (1H, s), 4.16 (2H, q, J=7 Hz), 3.64 (2H, s), 3.56 (3H, s), 1.2 (3H, t, J=7 Hz).

Ethyl 5-(4′-methylbenzoyl)-1-methyl-4-trifluoromethylpyrrole-2-acetate (20), ethyl 5-(4′-methoxybenzoyl)-1-methyl-4-trifluoromethylpyrrole-2-acetate (21), ethyl 5-(3′-trifluoromethylbenzoyl)-1-methyl-4-trifluoromethylpyrrole-2-acetate (22) and ethyl 5-(2′-thienoyl)-1-methyl-4-trifluoromethylpyrrole-2-acetate (23) are prepared analogously.

EXAMPLE 1

5-p-Chlorobenzoyl-1-methyl-4-trifluoromethylpyrrole-2-acetic acid (1)

The above ethyl ester (280 mg, 0.75 mmole) was refluxed in 10% aqueous sodium hydroxide (10 ml) and ethanol (3 ml) for 1 hour. The resulting solution was diluted with water (20 ml) and washed with ether (2×15 ml) before acidifying with dilute hydrochloric acid. The precipitate formed was extracted into ether (2×50 ml), the organic layer washed with water (2×50 ml), dried (anhydrous Na₂SO₄) and evaporated to dryness to leave a yellow oil. This was purified by recrystallisation from 1:2 chloroform:pentane to give the title compound as a pale yellow crystalline solid m.p. 129°–131° C., n.m.r. δ(CDCl₃) 10.60 (1H, s), 7.72 (2H, d, J=9 Hz), 7.34 (2H, d, J=9 Hz), 6.33 (1H, s), 3.68 (2H, s) and 3.55 (3H, s).

5-(3′-chlorobenzoyl)-1-methyl-4-trifluoromethylpyrrole-2-acetic acid (2) was prepared analogously.

n.m.r. δ(CDCl₃): 8.86 (1H, br, s), 7.9–7.15 (4H, m), 6.33 (1H, s), 3.72 (2H, s), 3.58 (3H, s).

5-(4′-methylbenzoyl)-1-methyl-4-trifluoromethylpyrrole acetic acid (3), 5-(4′-methoxybenzoyl)-1-methyl-4-trifluoromentylpyrrole acetic acid (4), 5-(3′-trifluoromethylbenzoyl)-1-methyl-4-trifluoromethylpyrrole acetic acid (5), and 5-(2′-thienoyl)-1-methyl-4-trifluoromethylpyrrole acetic acid (6) are prepared analogously.

EXAMPLE 2

4-[5′-(4″-chlorobenzoyl)-1′-methyl-4′-trifluoromethyl-2′-pyrryl]but-1-ene (7)

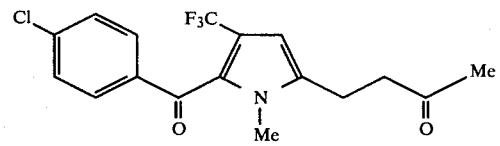

The acetic acid (1) (5.0 g, 0.0145 mole) was taken up in dry THF (50 ml) and added dropwise to a solution of di-isopropylamine (4.9 ml, 0.035 mole) and n-butyllithium (28 ml of 1.15 M sol., 0.032 mole) in dry THF (70 ml) under nitrogen at 0° C. The solution formed was then allowed to come to room temperature over 1½ hours before allyl bromide (1.25 ml, 0.0145 mole) was added. The reaction mixture was left stirring at room temperature for 2 hours. On cooling in an ice bath, water (100 ml) was added to the solution, which was then acidified with 5 N HCl acid. The product was extracted into ethyl acetate (3×100 ml), washed with water (2×100 ml), dried (anhydrous sodium sulphate) and evaporated to leave a black solid. The crude product was taken up in dry quinoline (10 ml) and together with copper bronze (0.5 g) was heated under nitrogen at about 200° C. for 1½ hours. On cooling, ethyl acetate (50 ml) was added and the mixture filtered and then washed with 5 N HCl acid, followed by water (2×50 ml), dried (anhydrous sodium sulphate) and evaporated to gave a black oil. The crude product was chromatographed on silica (200 g) using 1:1 petol:ether as eluant to afford a red oil (2.3 g, 46%). This was crystallised from ether:-pentane to give a yellow solid (7), n.m.r.: δ(CCl₄): 7.59 (2H, d, J=9 Hz), 7.24 (2H, d, J=9 Hz), 6.05 (1H, s), 5.4–5.9 (1H, m), 4.8–5.2 (2H, m), 3.50 (3H, s), 2.2–2.7 (4H, m).

4-[5′-(3″-chlorobenzoyl)-1′-methyl-4′-trifluoromethyl-2′-pyrryl]but-1-ene (8),

4-[5′-(4″-methylbenzoyl)-1′-methyl-4′-trifluoromethyl-2′-pyrryl]but-1-ene (9),

4-[5′-(4″-methoxybenzoyl)-1′-methyl-4′-trifluoromethyl-2′-pyrryl]but-1-ene (10), 4-[5′-(3″-trifluoromethylbenzoyl)-1′-methyl-4′-trifluoromethyl-2′-pyrryl]but-1-ene (11), and 4-[5′-(2″-thienoyl)-1′-methyl-4′-trifluoromethyl-2′-pyrryl]but-1-ene (12) are prepared analogously.

EXAMPLE 3

4-[5′-(4″-chlorobenzoyl)-1′-methyl-4′-trifluoromethyl-2′-pyroyl]butan-2-one (13)

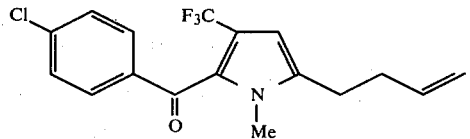

A solution of the butene (7) (0.80 g, 0.0023 mole) in DMF (1 ml) was added to a solution prepared by bubbling air through a stirred mixture of copper (I) chloride (0.30 g, 0.0030 mole) and palladium (II) chloride (0.10 g, 0.0006 mole) in DMF (3.5 ml) and water (0.35 ml) for 1½ hours. Air was bubbled through the resulting solution for a further 3½ hours. This solution was poured into water (100 ml) and extracted with ether (3×100 ml), washed with water (2×100 ml), dried and evaporated to give a brown oil. The crude product was chromatographed on silica (40 g) using 1:1 ether:petrol as eluant to afford a yellow solid (450 mg, 55%). This was recrystallised from ether petrol to give 4-[5′-(4″-chlorobenzoyl)-1′-methyl-4′-trifluoromethyl-2′-pyroyl]-butan-2-one (13) as a white solid (mp 87°–89° C.).

n.m.r. δ(CDCl₃): 7.67 (2H, d, J=9 Hz), 7.32 (2H, d, J=9 Hz), 6.07 (1H, s), 3.53 (3H, s), 2.82 (4H, s), 2.18 (3H, s).

4-[5′-(3″-chlorobenzoyl)-1′-methyl-4′-trifluoromethyl-2′-pyroyl]butan-2-one (14), 4-[5′-(4″-methylbenzoyl)-1′-methyl-4′-trifluoromethyl-2′-pyroyl]butan-2-one (15), 4-[5′-(4″-methoxybenzoyl)-1′-methyl-4′-trifluoromethyl-2′-pyroyl]butan-2-one (16), 4-[5′-(3″-trifluoromethylbenzoyl)-1′-methyl-4′-trifluoromethyl-2′-pyroyl]butan-2-one (17), 4-[5′-(2″-thienoyl)-1′-methyl-4′-trifluoromethyl-2′-pyroyl]butan-2-one (18) are prepared analogously.

Pharmacology

Analgesic Activity

The method used for determining analgesic activity was as follows:

Groups of 10 male T/O mice weighing between 20 and 25 g were injected intraperitoneally with 0.2 ml of a 0.02% solution of phenyl-p-quinone maintained at 37° C. The animals were observed for a subsequent 8 minutes and the number failing to 'writhe' within this period were considered to be showing an analgesic effect. Compounds were administered orally 1 hour prior to phenyl-p-quinone injection. The percentage of mice prevented from writhing in each group was plotted against dose of compound on log probit paper and the $ED_{50}$ was calculated by the method of Litchfield, J. T. and Wilcoxon, F. (1949), J. Pharmac. exp. Ther., 96 (2), 99–113.

The results of the test performed as described above were as follows:

| Compound | $ED_{50}$ mg/kg p.o. |
|---|---|
| (1) | 1.75 |
| No salt thereof | 1.6 |
| (13) | 25 |

Anti-inflammatory Activity

The sodium salt of compound (1) was tested for anti-inflammatory activity by the standard rat paw carrageenin-induced oedema test:

Groups of 8 male Wistar rats weighing between 120 and 165 g. were dosed orally with the compound 1 hr. before the sub-cutaneous injection of 0.1 ml 1.5% carrageenin into a paw to induce oedema. The duration of the oedema was 3–3½ hr. The significance of results was assessed by Student's 't' test.

The results were as follows:

| Dose mg/kg p.o. | % inhibition of oedema w.r.t. methylcellulose control |
|---|---|
| 15 | 30** |
| 5 | 25** |
| 1.67 | 18* |

**p < 0.001
*0.001 < p < 0.01
$ED_{25}$ 5.5 mg/kg p.o.

Toxicity

No toxic effects were observed in the above tests.
We claim:
1. A compound of the formula (I):

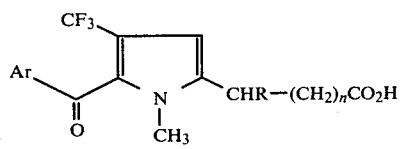

or a pharmaceutically acceptable salt or a pro-drug thereof, wherein:
Ar is phenyl unsubstituted or substituted by one or two moieties selected from halogen, $C_{1-4}$ alkyl, methoxy, methylthio or trifluoromethyl;
R is hydrogen or methyl; and
n is 0 or 1.
2. A compound according to claim 1 of the formula (VI):

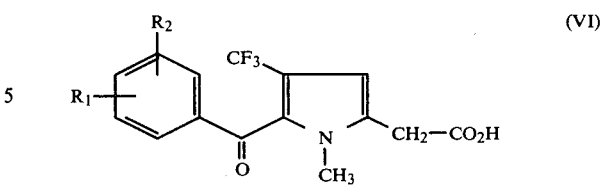

wherein the $R_1$ and $R_2$ are independently hydrogen, halogen, $C_{1-4}$ alkyl, methylthio or trifluoromethyl, or a pharmaceutically acceptable salt thereof or a pro-drug thereof of the formula (VII), (VIII), (IX) or (X)

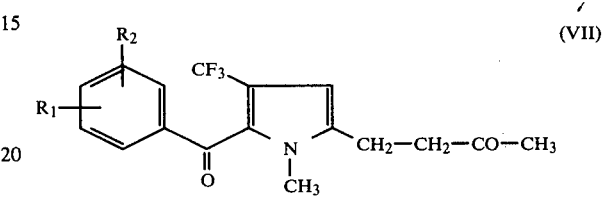

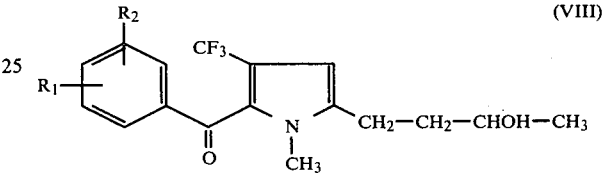

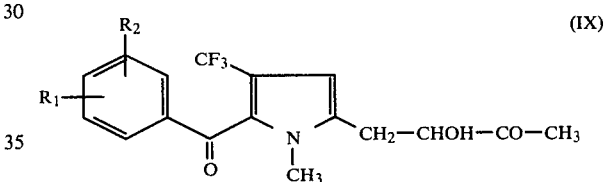

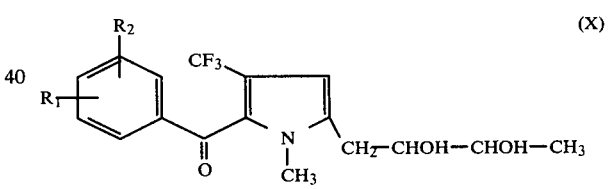

wherein the variables are as defined in claim 1.
3. 5-p-Chlorobenzoyl-1-methyl-4-trifluoromethylpyrrole-2-acetic acid,
5-(3'-chlorobenzoyl)-1-methyl-4-trifluoromethylpyrrole-2-acetic acid,
5-(4'-methylbenzoyl)-1-methyl-4-trifluoromethylpyrrole acetic acid,
5-(4'-methoxybenzoyl)-1-methyl-4-trifluoromethylpyrrole acetic acid,
5-(3'-trifluoromethylbenzoyl)-1-methyl-4-trifluoromethylpyrrole acetic acid,
4-[5'-(4''-chlorobenzoyl)-1'-methyl-4'-trifluoromethyl-2'-pyrryl]but-1-ene,
4-[5'-(3''-chlorobenzoyl)-1'-methyl-4'-trifluoromethyl-2'-pyrryl]but-1-ene,
4-[5'-(4''-methylbenzoyl)-1'-methyl-4'-trifluoromethyl-2'-pyrryl]but-1-ene,
4-[5'-(4''-methoxybenzoyl)-1'-methyl-4'-trifluoromethyl-2'-pyrryl]but-1-ene,
4-[5'-(3''-trifluoromethylbenzoyl)-1'-methyl-4'-trifluoromethyl-2'-pyrryl]but-1-ene,
4-[5'-(4''-chlorobenzoyl)-1'-methyl-4'-trifluoromethyl-2'-pyroyl]butan-2-one, 4-[5'-(3''-chlorobenzoyl)-1'-methyl-4'-trifluoromethyl-2'-pyroyl]butan-2-one, 4-[5'-(4''-methylbenzoyl)-1'-methyl-4'-trifluoromethyl-2'-pyroyl]butan-2-one, 4-[5'-(4''-methoxybenzoyl)-1'-methyl-4'-trifluoromethyl-2'-pyroyl]butan-2-one, 4-[5'-(3''-trifluoromethylbenzoyl)-1'-methyl-4'-trifluoromethyl-2'-pyroyl]butan-2-one, ethyl 5-(4'-methylbenzoyl)-1-methyl-4-trifluoromethylpyrrole-2-acetate, ethyl 5-(4'-methoxybenzoyl)-1-methyl-4-trifluoromethylpyrrole-2-acetate or ethyl 5-(3'-trifluoromethylbenzoyl)-1-methyl-4-trifluoromethylpyrrole-2-acetate 4. A prodrug of a compound of the formula (I) according to claim 1, wherein the $CO_2H$ group of the compound of the formula (I) is replaced by an in vivo hydrolysable ester or amide group, a CHO or $CH_2OH$ group or by a group selected from those of sub-formulae (a)-(k):

| | |
|---|---|
| $-CH_2-CO-CH_3$ | (a) |
| $-CH_2-CHOH-CH_3$ | (b) |
| $-CHOH-CHOH-CH_3$ | (c) |
| $-CHOH-CO-CH_3$ | (d) |
| $-CH_2-CH(OCOR_6)-CH_3$ | (e) |
| $-CH=C(OR_7)-CH_3$ | (f) |
| $-CH-C(OR_7)=CH_2$ | (g) |
| $-CH_2-C(OR_8)OR_9-CH_3$ | (h) |
| $-CH_2-C(OCOR_{10})=CH_2$ | (i) |
| $-CH=C(OCOR_{10})-CH_3$ | (j) |
| $-CH_2-CH=CH_2$ | (k) | wherein $R_6$ is phenyl, substituted phenyl or $C_{1-4}$ alkyl optionally substituted by optionally substituted phenyl or amino; $R_7$ is a $C_{1-4}$ alkyl group; $R_8$ and $R_9$ are each $C_{1-4}$ alkyl groups or are joined to represent a $CH_2CH_2$ or $CH_2CH_2CH_2$ group; and $R_{10}$ is a $C_{1-4}$ alkyl group.

5. An anti-inflammatory pharmaceutical composition comprising an anti-inflammatory effective amount of a compound according to claim 1 or a pharmaceutically acceptable salt or a prodrug thereof and a pharmaceutically acceptable carrier.

6. A method of treating inflammatory and/or painful conditions in mammals which comprises administering to the sufferer a therapeutically effective dose of a compound according to claim 1 or a pharmaceutically acceptable salt or a prodrug thereof.

* * * * *